United States Patent [19]

Newkirk

[11] Patent Number: 5,679,537
[45] Date of Patent: Oct. 21, 1997

[54] IMMUNOASSAYS FOR MEASURING THE AVIDITY OF RHEUMATOID FACTOR IN RHEUMATOID ARTHRITIS

[75] Inventor: Marianna M. Newkirk, Pierrefonds, Canada

[73] Assignee: McGill University, Montréal, Canada

[21] Appl. No.: 329,266

[22] Filed: Oct. 26, 1994

[51] Int. Cl.[6] .................................................. G01N 33/53
[52] U.S. Cl. ...................... 435/7.92; 435/7.95; 436/174; 436/512; 436/513; 436/518; 536/531
[58] Field of Search ................................. 435/7.92, 7.95, 435/7.1; 436/518, 531, 174, 811, 412, 427, 868, 512, 513

[56] References Cited

PUBLICATIONS

Abbas et al "Cellular and Molecular Immunology" ©1991 by W.B. Saunders Co, Philadelphia, PA pp. 53–55.
Newkirk, M.M. et al., 1993, *J. Rheumatol.*, 20:776–780.
Newkirk, M.M. et al., 1990, *Arthritis Rheum.*, 33:800.
Friguet, B. et al., 1985, *J. Immunol. Meth.*, 77:305–319.
Cashburn–Budd et al. 1992, *J. Rheumatol.* 19:1070–1074.
Young, A. et al., 1991, *Arthritis Rheum.*, 34:1425.
Van Zeben, D. et al., 1994, *Br. J. Rheumatol.*, 33:36–43.

*Primary Examiner*—Paula K. Hutzell
*Assistant Examiner*—Patricia A. Duffy
*Attorney, Agent, or Firm*—Swabey Ogilvy Renault

[57] ABSTRACT

The present invention relates to a novel immunoassay for measurement of rheumatoid factors (RFs) avidity for correlation with rheumatoid arthritis disease activity and for the presence of the different glycoforms of IgG.

3 Claims, 2 Drawing Sheets

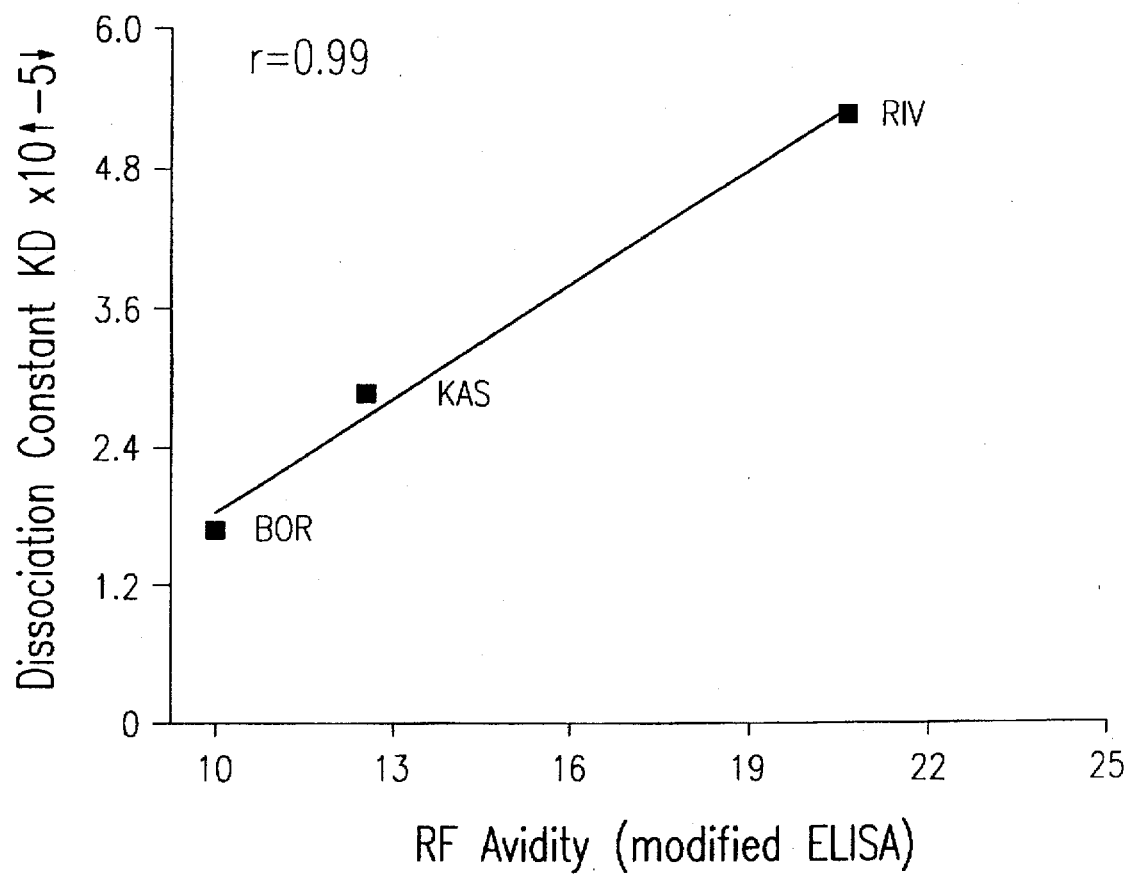
FIG_1

IMMUNOASSAYS FOR MEASURING THE AVIDITY OF RHEUMATOID FACTOR IN RHEUMATOID ARTHRITIS

BACKGROUND OF THE INVENTION (a) Field of the Invention

The invention relates to a novel ELISA immunoassay for measurement of rheumatoid factors (RFs) avidity for possible correlation with rheumatoid arthritis disease activity and for the presence of the different glycoforms of IgG.

(b) Description of Prior Art

Rheumatoid factors (RF) have long been suspected to play a role in the pathogenesis of rheumatoid arthritis (RA), as they are detected in up to 70% of RA patients and are sustained at high titers for years. Their association with the pathogenic changes have been controversial, and indeed they are found in normal individuals generally in low titers and in patients with mixed cryoglobulinemia frequently in high titers, who lack the synovitis characteristic of RA.

In the past decade, since the discovery of an imbalance of the different glycoforms of IgG in patients with RA, much research has focused on the possible consequences of one of the glycoforms of IgG, namely the Gal(0) form. Since the oligosaccharide chain on IgG resides in between the two gamma-2 domains, it has been postulated that changes in the structure such as the absence of the terminal sialic acid and galactose [gal(0)] could affect the binding of RFs since it is thought that they bind in the cleft between the gamma-2 and gamma-3 domains. It has been found that, whereas some purified monoclonal RFs bound maximally to IgG when the oligosaccharide chain was intact (Newkirk, M. M. et al., 1993, *J. Rheumatol.*, 20:776), other RFs bound even when the oligosaccharide was altered or removed (Newkirk, M. M. et al., 1990, *Arthritis Rheum.*, 33:800). These previous studies have all had the short coming that it was not known, which, if any, of the monoclonal antibodies studied, could be correlated with any pathogenic role.

It would be highly desirable to be provided with a simple assay for RFs which would allow the measurement of avidity in rheumatoid arthritis patients.

SUMMARY OF THE INVENTION

One aim of the present invention is to provide a simple assay for RFs which would allow the measurement of avidity in rheumatoid arthritis patients for correlation with rheumatoid arthritis disease activity and for the presence of the different glycoforms of IgG.

Another aim of the present invention is to provide for a method to identify patients with aggressive disease so that the clinician can modify the therapy.

In accordance with the present invention there is provided an ELISA immunoassay for measuring rheumatoid factors (RFs) avidity present in serum sample of rheumatoid arthritis patients, which comprises the steps of:

a) incubating a solid support coated with a human whole IgG antibody substantially specific for RFs or Fc fragments thereof, with serum or plasma sample from said patients for a time sufficient for an immunoreaction to occur between RFs present in said sample and said antibody or said Fc fragments thereof;

b) incubating said immunoreacted RFs with 2M guanidine HCl or 2M urea for a time sufficient to allow the release of low avidity RFs while high avidity RFs remain bound;

c) detecting the amount of bounded RFs by incubation with an enzyme labelled or chemically tagged F(ab')$_2$ fragments of anti-human IgG antibody specific for Fab, IgA or IgM antibody thereof for a time sufficient for an immunoreaction to occur followed by incubation with an enzyme substrate or an appropriate means to detect the tagged anti-human Ig;

whereby the avidity of the RFs present in said sample is calculated as the percent residual binding after step b) and whereby comparison with an avidity calibration curve obtained with a known amount of RFs allow the establishment of high avidity.

BRIEF DESCRIPTION OF THE DRAWINGS

FIG. 1 is a curve for the comparison of the avidity of three IgM monoclonal rheumatoid factors (RFs) for Fc from IgG1 as determined by the classical dissociation constant and the % residual RF binding after guanidine treatment;

DETAILED DESCRIPTION OF THE INVENTION

Figure 2A:
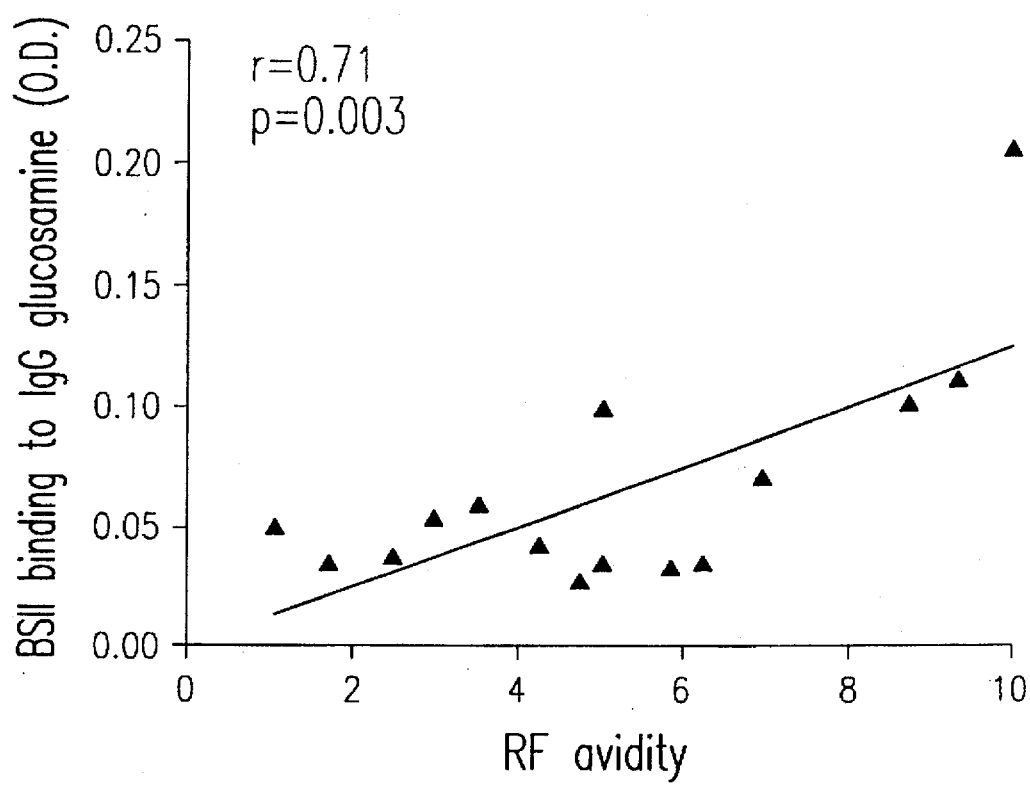
FIG. 2A is a linear correlation of RF avidity (% residual RF binding after guanidine treatment) and the binding of the lectin BSII to glucosamine on IgG from serum.

In accordance with the present invention, there is provided a new simple assay for rheumatoid factors (RFs) which allows the measurement of avidity for possible correlation with rheumatoid arthritis disease activity and for the presence of the different glycoforms of IgG.

In accordance with the present invention, the standard ELISA for measuring rheumatoid factor (RF) binding was modified with an additional step, namely a brief treatment with 2M guanidine, after the RF-Fc interaction, which allowed a measurement of the avidity of the interaction. Treatment with 4M guanidine eliminated RF binding. There was a direct correlation (r=0.99) between the avidity as measured by the modified guanidine ELISA, and the dissociation constant for monoclonal RFs, as measured by competitive ELISA.

Rheumatoid arthritis (RA) patients were tested for RF avidity using the modified ELISA of the present invention. Of the RF seropositive RA patients tested, 47% had RFs of high avidity ≧8% RF binding remaining after guanidine treatment (arbitrary cutoff). Tender joint count scores were significantly higher in the high avidity group (p=0.05), whereas there was no significant difference in the ages, disease duration, sedimentation rate, RF titer or serum Ig levels of the group with high avidity RF binding compared to those with low avidity. Additionally 58% of those with high avidity RFs had subcutaneous nodules, compared to 40% of the low avidity group. There was a significant increased number of nodules for the high avidity group compared to the low avidity group (p=0.03).

Interestingly, in studies of isolated immune complexes (IC), the RF avidity was significantly higher in the IC when compared to the circulating IgM RFs (p=0.01). Interestingly, and importantly the RF avidity correlated with the presence of the low galactose glycoform of IgG [gal(0)] in both circulating IgG and in IgG isolated from immune complexes (p=0.003 and 0.009 respectively). Information about the strength of binding to Fc identifies a subgroup of IgM RFs that are likely pathological in patients with RA, as well as a specific glycoform of the target antigen.

Patients

Patients with RA (70; 57 RF positive, 13 RF negative) were randomly selected from outpatient clinics at the Montreal General Hospital or a private clinic and all fulfilled the American College of Rheumatology (ACR) criteria. RF positivity was determined by laser nephelometry, and confirmed by ELISA. Only 5 of the patients had disease of less than three years in duration. The RA patients were investigated for a number of clinical criteria and all of the joint measurements were conducted by the same physician (JS).

RF avidity measurement

ELISA plates [EIA™ virgin polystyrene (critical to the assay), sold by ICN, Mississauga, ON] were coated with Fc fragments derived from a IgG1 myeloma protein at 5 ug/ml overnight in 15 mM sodium carbonate 35 mM sodium bicarbonate buffer, pH 9.6. After washing three times, 100 ul of the patients sera diluted 1:200 with PBS/Tween™ (0.14M sodium chloride, 1.4 mM potassium phosphate dibasic, 8 mM sodium phosphate, monobasic, 2.6 mM potassium chloride, 0.05% Tween™ 20) or positive (monoclonal IgM RFs) and negative (PBS/Tween™ only) controls, were added and the plate was incubated at 37° C. for 2 hrs. The plate was set up so that the top 4 rows were identical to the bottom 4 rows. After washing three times, 100 ul of 2M guanidine HCl (Sigma Chemicals, St. Louis, Mo.) in 50 mM Tris, pH 7.3, was added to the top four rows only, and incubated for 5 minutes at room temperature. The plates were washed a further three times, and 100 ul of F(ab')$_2$ fragments of peroxide conjugated donkey anti-human Fab chain (Jackson, West Grove ,Pa.), diluted 1:8000 in PBS was added. After a 1 hr incubation at 37° C., the plates were washed three times and the o-phenylamine diamine substrate was added. The reaction was stopped by the addition of 4M $H_2SO_4$ when sufficient colour developed or to a maximum of 30 minutes. The optical densities (OD) were read at 492 nm using an ELISA reader (SLT Lab instruments, model EAR 400RT™; Fisher Scientific, Montreal QC). Background binding was subtracted for both the guanidine treated and not treated wells using the respective PBS negative control. The percentage of RF binding remaining for the section of the plate treated with guanidine to the total RF binding in the absence of guanidine, was calculated and considered a measurement of avidity. Three control monoclonal RFs [BOR, KAS and RIV] were also tested, and the avidity for these RFs was compared to the dissociation constant calculated using a competition ELISA (Friguet, B. et al., 1985, *J. Immunol. Meth.*, 77:305).

Isolation of Immune Complexes

Plasma or serum (250 ul) from 15 of the patients which had been stored at −70° C. was incubated with an equal volume of 5% polyethylene glycol 8000 (PEG) (Fisher Chemicals) for >16 hrs at 4° C. After centrifugation of 13,000×g for 10 minutes, the pellet was washed once in 2.5% PEG, centrifuged and then resuspended in PBS. To remove the PEG, the samples were dialysed by Centricon™ (Amicon, Beverly, Mass.). Final volume of each sample was made to 500 ul.

Characterization of the oligosaccharide chains on IgG

A lectin binding ELISA was used to determine the terminal sugars on the oligosaccharide chains on IgG similar to that previously published by Casburn-Budd, R. et al. but with modifications (1992, *J. Rheumatol.* 19:1070). Circulating IgG, and IgG from immune complexes were examined. EIA plus (ICN) plates were coated with F(ab')$_2$ fragments of goat anti-IgG Feb (Jackson) at 2 ug/ml, overnight in carbonate/bicarbonate buffer, pH 9.6- After washing the plates 3 times with PBS-Tween™ 20, the IgG containing solutions were added (serum/plasma 1/400; immune complexes 1/25) and the plates were incubated for 1 hour at 37° C. After washing with PBS-Tween™ three times, the plates were incubated with 4M guanidine HCl in 50 mM Tris, pH 7.3 for 5 minutes at room temperature, and then washed three times with PBS-Tween™. The treatment with 4M guanidine HCl served two purposes, (1) to remove all bound RFs and to slightly unfold the Fc which made the oligosaccharide chains more accessible (important for the binding of the lectin BSII). The captured IgG was then incubated with biotinylated lectins (all from Vector, Burlingame, Calif.); EBL (Eldeberry Bark lectin, which binds sialic acid bound alpha 2,6 to galactose, diluted 1/2000 in PBS-Tween™); RCA (Ricinus communis agglutinin I which binds terminal galactose diluted 1/5000 in PBS-Tween™); or BSII (Bandeiraea simplicifolia lectin II which binds nonreducing terminal alpha or β-glucosamine, diluted 1/2000 in 10 mM HEPES, 0.15M NaCl, pH7.5; 0.05% Tween™ 20, containing 0.1 mM CaCl). After an incubation of 30 minutes at room temperature (RT) for EBL or RCA or 1 hr at 37° C. for BSII the plates were washed three times. Peroxidase conjugated avidin D (Vector), diluted 1/7000 in PBS, was added, and the plates were incubated for 30 minutes at RT. After washing three times the substrate was added as above.

To confirm the specificity of the lectin binding, inhibition studies were conducted using 0.2M D-galactose (for RCA) or N acetyl-D-glucosamine (for BSII) (EY Laboratories, San Mateo, Calif.). To monitor the effect of the guanidine HCl treatment on the captured IgG, the complexes were incubated with peroxidase conjugated anti-u (as above) or F(ab')$_2$ fragments of goat anti-gamma antibodies (1:8000 in PBS)(Tago, Burlingame, Calif.) in place of the lectins.

Avidity of RF binding in patients with RA

The apparent avidity as measured by the modified ELISA of the present invention was found to directly correlate with the dissociation constant for monoclonal RFs determined by the classical competition ELISA where r=0.99 (FIG. 1). For patients with RFs the mean RF avidity was 8.5±0.6 (range 0 to 24.1) whereas for those who had no detectable RF, there was no "RF" avidity measurable by the modified ELISA. When studying the sera of patients who have polyclonal antibodies present, it is important to determine a cutoff for RF positivity and, as well, to control for nonspecific binding to the plastic plate. Patient's whose IgM antibodies stick to the plastic plate can appear to have extremely high avidity binding but this can be ruled out with the appropriate controls. For example, sample X bound to the Fc+plastic and had a 0.123 O.D. in the absence of guanidine (below the cutoff for RF which was defined to be 0.3 O.D. for serum IgM), with 0.080 O.D. in the presence of guanidine, thus giving an apparent avidity of 65%. The same sample when incubated with the plastic plate in the absence of Fc gave virtually identical values. Since the initial O.D. was below the cut off for RF positivity, it was not considered RF positive and additionally the binding to plastic could account for the low O.D. both in the presence and absence of guanidine treatment.

For our study, of the samples found to be RF positive, an arbitrary value of 8% residual binding after 2M guanidine treatment (mean avidity of the RF positive patients) was chosen as a division between the high and low avidity binding RFs found in the serum of patients with RA. When so subdivided, as can be seen in Table 1 below, there was no difference in the age, disease duration or therapy of the two groups. Whereas the group with the high avidity RFs had a tendency towards more active disease, only the frequency and tender joint index as well as subcutaneous nodules were significantly higher (p=0.05 and 0.03 for tender joint index and subcutaneous nodules respectively). The RF titer was not significantly difference for the two groups. Extra-articular manifestations such as pulmonary function and sicca as measured by Schirmer's test were not different in the two groups. Interestingly, the ESR was elevated in both groups and appeared to be higher in the group with the low avidity RFs. Linear regression analysis of ESR and RF avidity for the two groups combined revealed a r=−0.36, p=0.008.

TABLE 1

Patient demographics and disease manifestations in RA patients with RFs of high or low avidity

| | IgM RF Avidity Group | |
|---|---|---|
| Feature | High (≧8[1]) | Low (<8) |
| Number (%) | 27 (47) | 30 (53) |
| Sex F:M | 19:8 | 25:5 |
| Age (years) | 61.4 ± 3.0 | 61.8 ± 2.5 |
| Disease duration | 14.1 ± 1.9 | 16.1 ± 2.0 |
| No. on prednisone | 9 | 12 |
| Tender joints | | |
| No. with/tested (%) | 24/26 (92) | 23/29 (79) |
| index | 14.0 ± 2.7 | 7.7 ± 1.8 |
| | | (p = 0.05[2]) |
| Swollen joint index | 11.4 ± 2.2 | 10.9 ± 2.0 |
| ESR mm/hr | 30.6 ± 2.8 | 38.0 ± 2.6 |
| Pulmonary function DCO[3] | 17.5 ± 1.2 | 17.8 ± 1.0 |
| Subcutaneous nodules | | |
| No. with/tested(%) | 14/24 (58) | 10/25 (40) |
| nodules (mean #) | 8.7 ± 3.5 | 5.4 ± 1.8 |
| | | (p = 0.03[2]) |
| Sicca | 15.2 ± 2.6 | 16.6 ± 2.2 |
| Schirmer's mm/5 min. | | |
| RF titer (chart) | 717.6 ± 136.7 | 429.6 ± 99.1 |
| (p = 0.09) | | |
| RF score (ELISA)[4] | 1.14 ± 0.10 | 0.98 ± 0.08 |
| Serum   IgG g/L | 11.9 ± 1.3 | 13.1 ± 0.9 |
|             IgA g/L | 2.63 ± 0.32 | 2.80 ± 0.30 |
|             IgM g/L | 1.40 ± 0.14 | 1.57 ± 0.11 |

[1]arbitrary division at 8% residual binding of RF after treatment with 2M guanidine;
[2]Mann Whitney U test;
[3]DCO, diffusing capacity of $CO_2$; and
[4]O.D. for sera diluted 1:200.

Although longitudinal studies were not conducted, four patients were serially sampled and in general, although there were minor changes in the IgM RF avidity with time (one patient with active disease had RF avidity values of 13, 8 and 9% sampled over a two year period), 3 of the 4 remained in either the high or low avidity groups when the 8% residual binding was used as a division. Additionally, 4 of 5 patients who had disease of less than 3 years duration had RFs in the high avidity group (RF avidity 10.1±1.1).

RF avidity in immune complexes

In studies of isolated immune complexes from 15 of the patients, the avidity of the RFs in the complexes was significantly higher than that for the paired serum RFs (mean RF avidity for IC was 7.66±1.01 and for serum 5.11±0.70, p=0.01).

Oligosaccharide chain characterization on IgG from serum and IC

The oligosaccharide chain on the IgG was characterized for both circulating IgG, and IgG in isolated immune complexes. Treatment with 4M guanidine to remove the IgM RFs from the complexes allowed the measurement of the oligosaccharide chains in IgG. As can be seen in Table 2 below, this treatment had little effect on the amount of the captured IgG (very high avidity interaction), but the lectin binding profile changed as seen with the RCA binding, likely reflecting the binding of the lectin to both IgG and IgM when the complexes were not treated with 4M guanidine. As can be seen, both the amount of IgM and the RF in the captured IgG immune complexes diminished with treatment of 2 and 4M guanidine.

TABLE 2

Binding of peroxidase conjugated antibodies or lectins to captured IgG and the detection of RFs, with and without treatment with guanidine HCl, in representative samples

| | | Binding to IgG IC[1] (O.D.) | | | | |
|---|---|---|---|---|---|---|
| sample IC or RF | guanidine HCl (M) | anti-gamma | anti-mu | RCA | IgM RF ELISA | Serum RF titer |
| IC-3 | 0 | 0.880 | 1.277 | 0.850 | 0.602 | NA |
|  | 2 | NA[2] | 1.010 | 0.731 | 0.066 |  |
|  | 4 | 0.900 | 0.259 | 0.524 | 0 |  |
| IC-7 | 0 | 0.909 | 0.247 | 0.457 | 0.171 | 604 |
|  | 2 | NA | 0.215 | 0.665 | 0 |  |
|  | 4 | 0.841 | 0.100 | 0.692 | 0 |  |
| IC-9 | 0 | 0.864 | 0.198 | 0.243 | 0.622 | 1026 |
|  | 2 | NA | 0.140 | 0.349 | 0.031 |  |
|  | 4 | 0.827 | 0.080 | 0.304 | 0 |  |
| IC-20 | 0 | 0.878 | 1.590 | 1.442 | 0.827 | 1649 |
|  | 2 | NA | 1.259 | 0.915 | 0.147 |  |
|  | 4 | 0.899 | 0.031 | 0.680 | 0 |  |
| BOR[3] | 0 |  |  |  | 0.769 |  |
|  | 2 |  |  |  | 0.075 |  |
|  | 3 |  |  |  | 0 |  |
|  | 4 |  |  |  | 0 |  |
| RIV[3] | 0 |  |  |  | 1.149 |  |
|  | 2 |  |  |  | 0.314 |  |
|  | 3 |  |  |  | 0.019 |  |
|  | 4 |  |  |  | 0 |  |

[1]immune complexes (IC) captured via IgG on ELISA plate, subsequent binding of peroxidase conjugated anti-gamma, anti-mu or biotinylated RCA, as in methods;
[2]not available; and
[3]monoclonal IgM RFs, at 0.5 ug/ml.
All values are means of duplicates, with background subtracted.

Figure 2B:
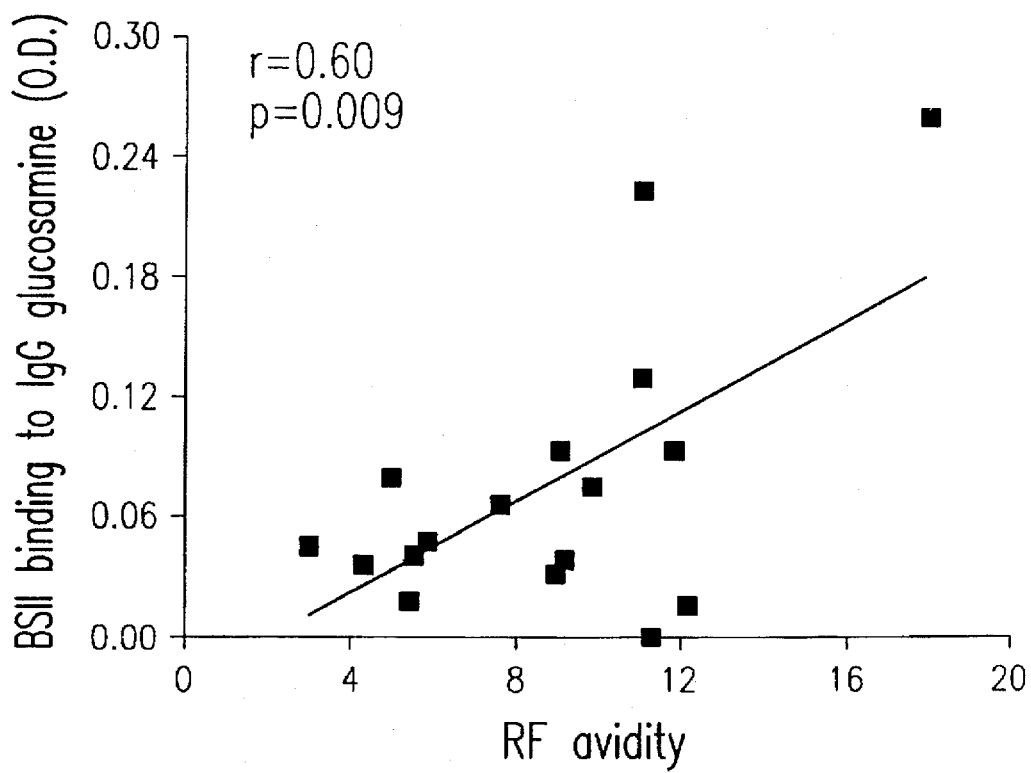
FIG. 2B is a linear correlation of RF avidity (% residual RF binding after guanidine treatment) and the binding of the lectin BSII to glucosamine on IgG from isolated immune complexes.

Interestingly, the avidity of the RFs was found to significantly correlate with the low galactose glycoform of IgG (after 4M guanidine treatment) as can be seen in FIGS. 2A and 2B. The binding of BSII to the terminal glucosamine indicates the absence of galactose, thus identifying the Gal(o) glycoform. This binding was inhibited the incubation with N-acetyl glucosamine. Although there was a negative r value (r=−0.15) for the correlation of RF avidity with the binding of the lectin RCA to the IgG (direct measurement of galactose) it was not significant. Similarly, the correlation of sialic acid on the IgG in the immune complexes with the RF avidity had an r=−0.33 but was not significant.

In accordance with the present invention, there is provided a simple modification of the standard ELISA used to detect RFs, which allows the measurement of the avidity of the interaction, and compares very well with the classical dissociation constant as measured for monoclonal RFs. The assay is simple and reproducible, but is dependent on the type of ELISA plate used and conditions must be established for individual plastics. The brief 2M guanidine treatment, known to cause proteins to slightly unfold, allowed the dissociation of the low avidity interactions, yet retain the higher avidity binding. At higher concentrations (4M) RFs could be entirely stripped off the Fc on the plate. This assay has enabled us to investigate the nature of the avidity of polyclonal IgM RFs in serum and immune complexes of patients with RA and re-evaluate the correlations of high avidity RFs with disease parameters.

It was found that the high avidity RFs correlated with both the articular damage and with one extra articular feature, namely subcutaneous nodules suggesting a possible role of these RFs in the pathogenesis of these features but with less impact on such things as compromised pulmonary function or sicca symptoms. No previous study has investigated the role of RF avidity and any pathological associations. There have, however, been many previous studies which have investigated the different subclasses of RF and their associations with disease manifestations, with in many cases conflicting findings. Most previous studies have shown that IgM RFs (not subdivided according to avidity) do not correlate with bone erosions, disease activity, or other extra-articular manifestations in patients with RA, but that IgA and/or IgG RFs do. These latter assays, however, are not routinely used to either diagnose or monitor patients with RA, in part due to technical difficulties. Since vasculitis is rarely seen in the patient population in Montreal, no comparitive studies with RF avidity were possible.

Our finding that the avidity of the RF interaction with Fc correlated with the gal(o) glycoform of IgG in both serum and immune complexes suggests that there is a subpopulation of IgM RFs that likely bind with high avidity to this glycoform. A caveat must be considered, as the lectin assay does not discriminate between the oligosaccharide in the Fc region from that in the Fab region. Although the percentage of antibody molecules that have an oligosaccharide chain in the variable region is unknown (likely about 30%), studies have previously shown that the oligosaccharide in the Fab region predominantly terminates in sialic acid, whereas the carbohydrate chain in the Fc is much more variable. Thus it is highly likely that the changes that have been detected in our study in the amount of glucosamine [gal(o)] reflect the oligosaccharide in the Fc region.

It is interesting that the low galactose glycoform of IgG has been previously shown to both aid in the diagnosis of RA (Young, A. et al., 1991, *Arthritis Rheum.*, 34:1425) and predict a more progressive disease course (Van Zeben, D. et al., 1994, *Br. J. Rheumatol.*, 33:36). In an animal model of arthritis it has been shown that the agalactosyl glycoform of IgG is pathogenic. It is possible that the presence of elevated amounts of the low galactose glycoform in RA patients identifies those that have IgM RFs with high avidity.

Further studies are needed to determine whether the identification of high avidity IgM RFs in early disease will predict erosive disease. It is possible that with the identification of individuals with high avidity RFs, a more aggressive therapy in these individuals may be warranted to help to alleviate the potential damage.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

I claim:

1. An immunoassay for measuring the avidity of rheumatoid factors (RFs) present in a serum or plasma sample of a rheumatoid arthritis patient, which comprises the steps of:

a) incubating a virgin polystyrene plate coated with a whole IgG antibody or Fc fragments thereof, with a serum or plasma sample from said patient for a time sufficient for RFs present in said sample to specifically bind said antibody or said Fc fragments thereof;

b) incubating a first part of said immunoreacted sample RFs with 2M guanidine HCl or 2M urea for 5 minutes to allow the release of low avidity RFs while high avidity RFs remain bound, and maintaining a second part of said immunoreacted sample RFs which is not treated;

c) detecting the amount of bound RFs in the second part of said immunoreacted sample RFs not treated in step b) and in the first part of said immunoreacted sample RFs incubated with guanidine HCl or urea in step b) by incubation with an enzyme labeled or chemically tagged F(ab')$_2$ fragments of anti-human IgG, IgA or IgM antibody which specifically binds Fab of the RFs for a time sufficient for an immunoreaction to occur followed by incubation with an enzyme substrate or an appropriate means to detect the tagged anti-human F(ab')$_2$ fragments; and d) measuring percent residual binding as a measure of avidity of the RFs present in said sample by dividing the amount of guanidine incubated sample by the amount of the non-treated sample.

2. The immunoassay of claim 1, wherein said anti-human IgG, IgA or IgM antibody is conjugated with peroxide and said enzyme substrate is o-phenylamine diamine.

3. The immunoassay of claim 2, wherein said detecting is effected by reading the optical density.

* * * * *